(12) United States Patent
Glerum et al.

(10) Patent No.: US 9,211,196 B2
(45) Date of Patent: Dec. 15, 2015

(54) EXPANDABLE FUSION DEVICE AND METHOD OF INSTALLATION THEREOF

(75) Inventors: Chad Glerum, Pennsburg, PA (US); Sean Suh, Plymouth Meeting, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 13/403,349

(22) Filed: Feb. 23, 2012

(65) Prior Publication Data

US 2012/0158146 A1 Jun. 21, 2012

Related U.S. Application Data

(63) Continuation of application No. 13/273,994, filed on Oct. 14, 2011, which is a continuation of application No. 12/579,833, filed on Oct. 15, 2009, now Pat. No. 8,062,375.

(51) Int. Cl.
*A61F 2/44* (2006.01)
*A61F 2/30* (2006.01)
*A61F 2/46* (2006.01)

(52) U.S. Cl.
CPC ............... *A61F 2/447* (2013.01); *A61F 2/4611* (2013.01); *A61F 2002/3008* (2013.01); *A61F 2002/3052* (2013.01); *A61F 2002/3055* (2013.01); *A61F 2002/3093* (2013.01); *A61F 2002/30387* (2013.01); *A61F 2002/30448* (2013.01); *A61F 2002/30492* (2013.01); *A61F 2002/30507* (2013.01); *A61F 2002/30515* (2013.01); *A61F 2002/30523* (2013.01); *A61F 2002/30556* (2013.01); *A61F 2002/30579* (2013.01);

(Continued)

(58) Field of Classification Search
CPC .................. A61F 2/4455; A61F 2/447; A61F 2002/3052; A61F 2002/30579
USPC .................................. 623/17.11, 17.15, 17.16
See application file for complete search history.

(56) References Cited

U.S. PATENT DOCUMENTS 4,349,921 A 9/1982 Kuntz
4,599,086 A 7/1986 Doty
(Continued)

FOREIGN PATENT DOCUMENTS

DE 4012622 C1 7/1991
DE 4327054 C1 4/1995
(Continued)

OTHER PUBLICATIONS

International Search Report and Written Opinion in related PCT application—PCT/US2010/052791.
(Continued)

*Primary Examiner* — Jan Christopher Merene
*Assistant Examiner* — Atiya Mahmud

(57) ABSTRACT

The present invention provides an expandable fusion device capable of being installed inside an intervertebral disc space to maintain normal disc spacing and restore spinal stability, thereby facilitating an intervertebral fusion. In one embodiment, the fusion device includes a body portion, a first endplate, and a second endplate, the first and second endplates capable of being moved in a direction away from the body portion into an expanded configuration or capable of being moved towards the body portion into an unexpanded configuration. The fusion device is capable of being deployed and installed in both configurations.

13 Claims, 8 Drawing Sheets

(52) U.S. Cl.
CPC ............... *A61F2002/30622* (2013.01); *A61F 2002/30777* (2013.01); *A61F 2002/30878* (2013.01); *A61F 2002/30904* (2013.01); *A61F 2002/448* (2013.01); *A61F 2002/4475* (2013.01); *A61F 2002/4629* (2013.01); *A61F 2002/4677* (2013.01); *A61F 2220/005* (2013.01); *A61F 2220/0025* (2013.01); *A61F 2250/0098* (2013.01); *A61F 2310/00017* (2013.01); *A61F 2310/00023* (2013.01); *A61F 2310/00976* (2013.01)

(56) References Cited

U.S. PATENT DOCUMENTS

| | | | | |
|---|---|---|---|---|
| 4,863,476 | A | 9/1989 | Shepperd | |
| 4,863,477 | A | 9/1989 | Monson | |
| 5,123,926 | A | 6/1992 | Pisharodi | |
| 5,290,312 | A | 3/1994 | Kojimoto et al. | |
| 5,306,310 | A | 4/1994 | Siebels | |
| 5,375,823 | A | 12/1994 | Navas | |
| 5,390,683 | A | 2/1995 | Pisharodi | |
| 5,522,899 | A | 6/1996 | Michelson | |
| 5,534,030 | A | 7/1996 | Navarro et al. | |
| 5,554,191 | A | 9/1996 | Lahille et al. | |
| 5,571,192 | A | 11/1996 | Schonhoffer | |
| 5,645,596 | A | 7/1997 | Kim | |
| 5,653,763 | A | 8/1997 | Errico et al. | |
| 5,665,122 | A | 9/1997 | Kambin | |
| 5,676,701 | A | 10/1997 | Yuan et al. | |
| 6,039,761 | A | 3/2000 | Li et al. | |
| 6,045,579 | A | 4/2000 | Hochshuler et al. | |
| 6,080,193 | A | 6/2000 | Hochshuler | |
| 6,099,531 | A | 8/2000 | Bonutti | |
| 6,126,689 | A | 10/2000 | Brett | |
| 6,176,882 | B1 | 1/2001 | Biedermann | |
| 6,258,125 | B1 | 7/2001 | Paul et al. | |
| 6,454,807 | B1* | 9/2002 | Jackson | 623/17.15 |
| 6,554,863 | B2 | 4/2003 | Paul et al. | |
| 6,558,423 | B1 | 5/2003 | Michelson | |
| 6,562,074 | B2 | 5/2003 | Gerbec et al. | |
| 6,576,016 | B1 | 6/2003 | Hochshuler et al. | |
| 6,641,614 | B1 | 11/2003 | Wagner et al. | |
| 6,648,917 | B2 | 11/2003 | Gerbec et al. | |
| 6,666,891 | B2 | 12/2003 | Boehm, Jr. et al. | |
| 6,692,495 | B1 | 2/2004 | Zacouto | |
| 6,706,070 | B1 | 3/2004 | Wagner et al. | |
| 6,752,832 | B2 | 6/2004 | Neumann | |
| 6,814,756 | B1 | 11/2004 | Michelson | |
| 6,830,589 | B2 | 12/2004 | Erickson | |
| 6,849,093 | B2 | 2/2005 | Michelson | |
| 6,852,129 | B2 | 2/2005 | Gerbec et al. | |
| 6,863,673 | B2 | 3/2005 | Gerbec et al. | |
| 6,881,228 | B2 | 4/2005 | Zdeblick et al. | |
| 7,018,415 | B1 | 3/2006 | McKay | |
| 7,070,598 | B2 | 7/2006 | Lim et al. | |
| 7,204,853 | B2 | 4/2007 | Gordon et al. | |
| 7,217,291 | B2 | 5/2007 | Zucherman et al. | |
| 7,282,063 | B2 | 10/2007 | Cohen et al. | |
| 7,316,714 | B2 | 1/2008 | Gordon et al. | |
| 7,473,276 | B2 | 1/2009 | Aebi et al. | |
| 7,547,325 | B2 | 6/2009 | Biedermann et al. | |
| 7,621,953 | B2 | 11/2009 | Braddock, Jr. et al. | |
| 7,641,693 | B2 | 1/2010 | Gutlin et al. | |
| 7,682,396 | B2 | 3/2010 | Beaurain et al. | |
| 7,749,270 | B2 | 7/2010 | Peterman | |
| 7,753,958 | B2 | 7/2010 | Gordon et al. | |
| 7,771,473 | B2 | 8/2010 | Thramann | |
| 7,780,732 | B2 | 8/2010 | Abernathie | |
| 7,799,081 | B2 | 9/2010 | McKinley | |
| 7,815,683 | B2 | 10/2010 | Melkent et al. | |
| 7,837,734 | B2 | 11/2010 | Zucherman et al. | |
| 7,875,078 | B2 | 1/2011 | Wysocki et al. | |
| 7,901,409 | B2 | 3/2011 | Canaveral et al. | |
| 7,909,869 | B2 | 3/2011 | Gordon et al. | |
| 7,951,199 | B2 | 5/2011 | Miller | |
| 8,062,375 | B2 | 11/2011 | Glerum | |
| 8,123,810 | B2 | 2/2012 | Gordon et al. | |
| 8,137,405 | B2 | 3/2012 | Kostuik | |
| 8,454,617 | B2* | 6/2013 | Schaller et al. | 606/90 |
| 8,647,386 | B2 | 2/2014 | Gordon et al. | |
| 2002/0045945 | A1 | 4/2002 | Liu | |
| 2002/0068976 | A1 | 6/2002 | Jackson | |
| 2002/0068977 | A1 | 6/2002 | Jackson | |
| 2004/0030387 | A1 | 2/2004 | Landry | |
| 2004/0049271 | A1 | 3/2004 | Biedermann | |
| 2004/0054412 | A1 | 3/2004 | Gerbec et al. | |
| 2004/0087947 | A1* | 5/2004 | Lim et al. | 606/61 |
| 2004/0153065 | A1 | 8/2004 | Lim | |
| 2005/0021041 | A1 | 1/2005 | Michelson | |
| 2005/0021145 | A1 | 1/2005 | de Villiers | |
| 2005/0033432 | A1 | 2/2005 | Gordon | |
| 2005/0080422 | A1 | 4/2005 | Otte | |
| 2005/0113916 | A1 | 5/2005 | Branch, Jr. | |
| 2005/0149188 | A1 | 7/2005 | Cook | |
| 2005/0171541 | A1 | 8/2005 | Boehm | |
| 2005/0251258 | A1 | 11/2005 | Jackson | |
| 2005/0273171 | A1 | 12/2005 | Gordon | |
| 2005/0273174 | A1 | 12/2005 | Gordon | |
| 2005/0278026 | A1 | 12/2005 | Gordon | |
| 2005/0283244 | A1 | 12/2005 | Gordon | |
| 2005/0283245 | A1 | 12/2005 | Gordon | |
| 2006/0004453 | A1 | 1/2006 | Bartish, Jr. et al. | |
| 2006/0015184 | A1 | 1/2006 | Winterbottom | |
| 2006/0058876 | A1* | 3/2006 | McKinley | 623/17.11 |
| 2006/0058878 | A1 | 3/2006 | Michelson | |
| 2006/0084986 | A1 | 4/2006 | Grinberg | |
| 2006/0122701 | A1 | 6/2006 | Kiester | |
| 2006/0129244 | A1 | 6/2006 | Ensign | |
| 2006/0142859 | A1 | 6/2006 | McLuen | |
| 2006/0149385 | A1 | 7/2006 | McKay | |
| 2006/0195192 | A1 | 8/2006 | Gordon et al. | |
| 2006/0206207 | A1* | 9/2006 | Dryer et al. | 623/17.11 |
| 2006/0229729 | A1 | 10/2006 | Gordon et al. | |
| 2006/0241770 | A1 | 10/2006 | Rhoda | |
| 2006/0253201 | A1 | 11/2006 | McLuen | |
| 2007/0043442 | A1 | 2/2007 | Abernathie et al. | |
| 2007/0050030 | A1 | 3/2007 | Kim | |
| 2007/0050032 | A1 | 3/2007 | Gittings et al. | |
| 2007/0055377 | A1 | 3/2007 | Hanson et al. | |
| 2007/0191951 | A1 | 8/2007 | Branch, Jr. | |
| 2007/0255415 | A1 | 11/2007 | Edie et al. | |
| 2007/0270954 | A1* | 11/2007 | Wu | 623/17.11 |
| 2007/0270963 | A1* | 11/2007 | Melkent et al. | 623/17.11 |
| 2007/0270968 | A1 | 11/2007 | Baynham | |
| 2008/0021559 | A1 | 1/2008 | Thramann | |
| 2008/0065222 | A1 | 3/2008 | Hamada | |
| 2008/0114467 | A1 | 5/2008 | Capote | |
| 2008/0140207 | A1* | 6/2008 | Olmos et al. | 623/17.16 |
| 2008/0147193 | A1* | 6/2008 | Matthis et al. | 623/17.16 |
| 2008/0147194 | A1 | 6/2008 | Grotz | |
| 2008/0167657 | A1 | 7/2008 | Greenhalgh et al. | |
| 2008/0183204 | A1 | 7/2008 | Greenhalgh et al. | |
| 2008/0221694 | A1 | 9/2008 | Warnick | |
| 2008/0275455 | A1 | 11/2008 | Berry et al. | |
| 2008/0281346 | A1 | 11/2008 | Greenhalgh et al. | |
| 2008/0288073 | A1 | 11/2008 | Renganath et al. | |
| 2008/0300598 | A1 | 12/2008 | Barreiro et al. | |
| 2008/0306488 | A1 | 12/2008 | Altarac et al. | |
| 2008/0319487 | A1 | 12/2008 | Fielding et al. | |
| 2008/0319549 | A1 | 12/2008 | Greenhalgh et al. | |
| 2009/0024217 | A1 | 1/2009 | Levy | |
| 2009/0076616 | A1 | 3/2009 | Duggal | |
| 2009/0125062 | A1 | 5/2009 | Arnin | |
| 2009/0149956 | A1 | 6/2009 | Greenhalgh et al. | |
| 2009/0149959 | A1 | 6/2009 | Conner et al. | |
| 2009/0204218 | A1 | 8/2009 | Richelsoph | |
| 2009/0222100 | A1 | 9/2009 | Cipoletti et al. | |
| 2009/0240334 | A1 | 9/2009 | Richelsoph | |
| 2009/0270989 | A1 | 10/2009 | Conner et al. | |
| 2009/0281628 | A1 | 11/2009 | Oglaza et al. | |
| 2009/0292361 | A1* | 11/2009 | Lopez | 623/17.15 |
| 2009/0299478 | A1 | 12/2009 | Carls et al. | |
| 2009/0312763 | A1 | 12/2009 | McCormack et al. | |

(56) References Cited

U.S. PATENT DOCUMENTS

| | | |
|---|---|---|
| 2010/0049324 A1 | 2/2010 | Valdevit |
| 2010/0070041 A1 | 3/2010 | Peterman et al. |
| 2010/0082109 A1 | 4/2010 | Greenhalgh et al. |
| 2010/0179657 A1 | 7/2010 | Greenhalgh et al. |
| 2010/0185291 A1 | 7/2010 | Jimenez |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0222816 A1 | 9/2010 | Gabelberger |
| 2010/0222884 A1 | 9/2010 | Greenhalgh |
| 2010/0234952 A1 | 9/2010 | Peterman |
| 2010/0249933 A1 | 9/2010 | Trieu |
| 2010/0280622 A1 | 11/2010 | Mckinley |
| 2010/0286779 A1 | 11/2010 | Thibodeau |
| 2010/0286780 A1 | 11/2010 | Dryer |
| 2010/0286783 A1 | 11/2010 | Lechmann |
| 2010/0292796 A1 | 11/2010 | Greenhalgh |
| 2010/0305705 A1 | 12/2010 | Butler |
| 2010/0331981 A1 | 12/2010 | Mohammed |
| 2010/0331985 A1 | 12/2010 | Gordon |
| 2011/0035011 A1 | 2/2011 | Cain |
| 2011/0093074 A1 | 4/2011 | Glerum |
| 2011/0160861 A1 | 6/2011 | Jimenez |
| 2011/0172774 A1 | 7/2011 | Varela |
| 2011/0276142 A1 | 11/2011 | Niemiec |
| 2011/0301713 A1 | 12/2011 | Theofilos |
| 2011/0319997 A1 | 12/2011 | Glerum |
| 2012/0035729 A1 | 2/2012 | Glerum |
| 2012/0059470 A1 | 3/2012 | Weiman |
| 2012/0059472 A1 | 3/2012 | Weiman |
| 2012/0109308 A1 | 5/2012 | Lechmann |
| 2012/0130496 A1 | 5/2012 | Duffield |
| 2012/0165945 A1 | 6/2012 | Hansell |
| 2012/0185049 A1 | 7/2012 | Varela |
| 2012/0209386 A1 | 8/2012 | Triplett |
| 2012/0215313 A1 | 8/2012 | Saidha |
| 2012/0265309 A1 | 10/2012 | Glerum |
| 2012/0277870 A1 | 11/2012 | Wolters |
| 2012/0323329 A1 | 12/2012 | Jimenez |
| 2012/0330426 A1 | 12/2012 | McLaughlin |
| 2013/0023993 A1 | 1/2013 | Weiman |
| 2013/0023994 A1 | 1/2013 | Glerum |
| 2013/0158669 A1 | 6/2013 | Sungarian |

FOREIGN PATENT DOCUMENTS

| | | | |
|---|---|---|---|
| EP | 0576379 B1 | 6/1993 | |
| EP | 0610837 B1 | 7/1994 | |
| FR | 2794968 | 12/2000 | |
| JP | 2000-513263 | 10/2000 | |
| SU | 1424826 A1 | 9/1988 | |
| WO | 9201428 A1 | 2/1992 | |
| WO | 9525485 A1 | 9/1995 | |
| WO | 9942062 A1 | 8/1999 | |
| WO | 9966867 A1 | 12/1999 | |
| WO | 0245625 A1 | 6/2002 | |
| WO | 2004019829 A1 | 3/2004 | |
| WO | 2004069033 A2 | 8/2004 | |
| WO | 2006045094 A2 | 10/2005 | |
| WO | 2006045094 A2 | 4/2006 | |
| WO | 2006047587 A2 | 5/2006 | |
| WO | 2006113080 A2 | 10/2006 | |
| WO | 2008044057 A1 | 10/2007 | |
| WO | 2008044057 A1 | 4/2008 | |
| WO | WO 2008-044057 A1 | 4/2008 | |
| WO | 2008134515 A1 | 11/2008 | |
| WO | 2009114381 A1 | 9/2009 | |
| WO | WO 2009/124269 A1 * | 10/2009 | ............... A61F 2/30 |
| WO | 2012031267 A1 | 3/2012 | |

OTHER PUBLICATIONS

IPRP in related PCT application—PCT/US2010/052791.

* cited by examiner

EXPANDABLE FUSION DEVICE AND METHOD OF INSTALLATION THEREOF

FIELD OF THE INVENTION

This Patent Application is a continuation application claiming priority to U.S. patent application Ser. No. 13/273,994, filed Oct. 14, 2011, which is a continuation of U.S. patent application Ser. No. 12/579,833, filed Oct. 15, 2009 and now issued as U.S. Pat. No. 8,062,375, the entire contents of which are incorporated by reference.

FIELD OF THE INVENTION

The present invention relates to the apparatus and method for promoting an intervertebral fusion, and more particularly relates to an expandable fusion device capable of being inserted between adjacent vertebrae to facilitate the fusion process.

BACKGROUND OF THE INVENTION

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together, alleviating the associated pain.

However, there are drawbacks associated with the known conventional fusion devices and methodologies. For example, present methods for installing a conventional fusion device often require that the adjacent vertebral bodies be distracted to restore a diseased disc space to its normal or healthy height prior to implantation of the fusion device. In order to maintain this height once the fusion device is inserted, the fusion device is usually dimensioned larger in height than the initial distraction height. This difference in height can make it difficult for a surgeon to install the fusion device in the distracted intervertebral space.

As such, there exists a need for a fusion device capable of being installed inside an intervertebral disc space at a minimum to no distraction height and for a fusion device that can maintain a normal distance between adjacent vertebral bodies when implanted.

SUMMARY OF THE INVENTION

In an exemplary embodiment, the present invention provides an expandable fusion device capable of being installed inside an intervertebral disc space to maintain normal disc spacing and restore spinal stability, thereby facilitating an intervertebral fusion. In one embodiment, the fusion device includes a body portion, a first endplate, and a second endplate. The first and second endplates are capable of being moved in a direction away from the body portion into an expanded configuration or capable of being moved towards the body portion into an unexpanded configuration. The expandable fusion device is capable of being deployed and installed in the unexpanded configuration or the expanded configuration.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 1:
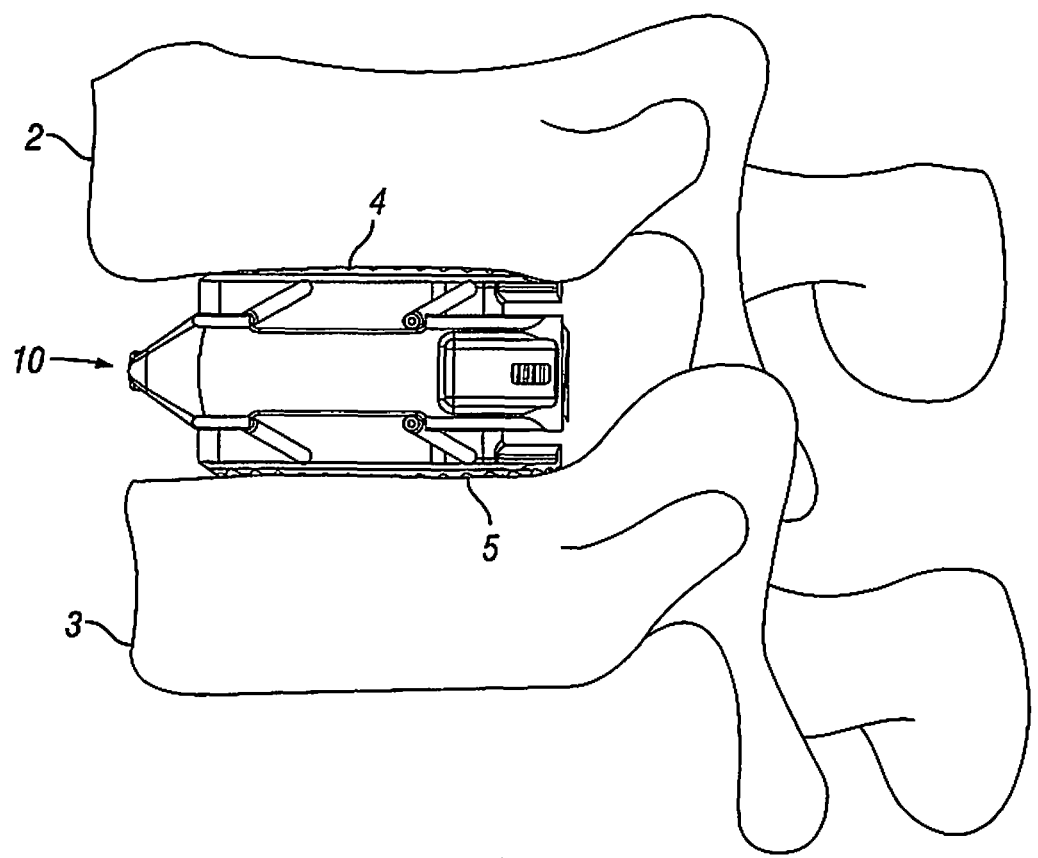
FIG. 1 is a side view of an embodiment of an expandable fusion device shown between adjacent vertebrae according to the present invention.

A spinal fusion is typically employed to eliminate pain caused by the motion of degenerated disk material. Upon successful fusion, a fusion device becomes permanently fixed within the intervertebral disc space. Looking at FIG. 1, an exemplary embodiment of an expandable fusion device 10 is shown between adjacent vertebral bodies 2 and 3. The fusion device 10 engages the endplates 4 and 5 of the adjacent vertebral bodies 2 and 3 and, in the installed position, maintains normal intervertebral disc spacing and restores spinal stability, thereby facilitating an intervertebral fusion. The expandable fusion device 10 can be manufactured from a number of materials including titanium, stainless steel, titanium alloys, non-titanium metallic alloys, polymeric materials, plastics, plastic composites, PEEK, ceramic, and elastic materials.

In an exemplary embodiment, bone graft or similar bone growth inducing material can be introduced around and within the fusion device 10 to further promote and facilitate the intervertebral fusion. The fusion device 10, in one embodiment, is preferably packed with bone graft or similar bone growth inducing material to promote the growth of bone through and around the fusion device. Such bone graft may be packed between the endplates of the adjacent vertebral bodies prior to, subsequent to, or during implantation of the fusion device.

Figure 2:
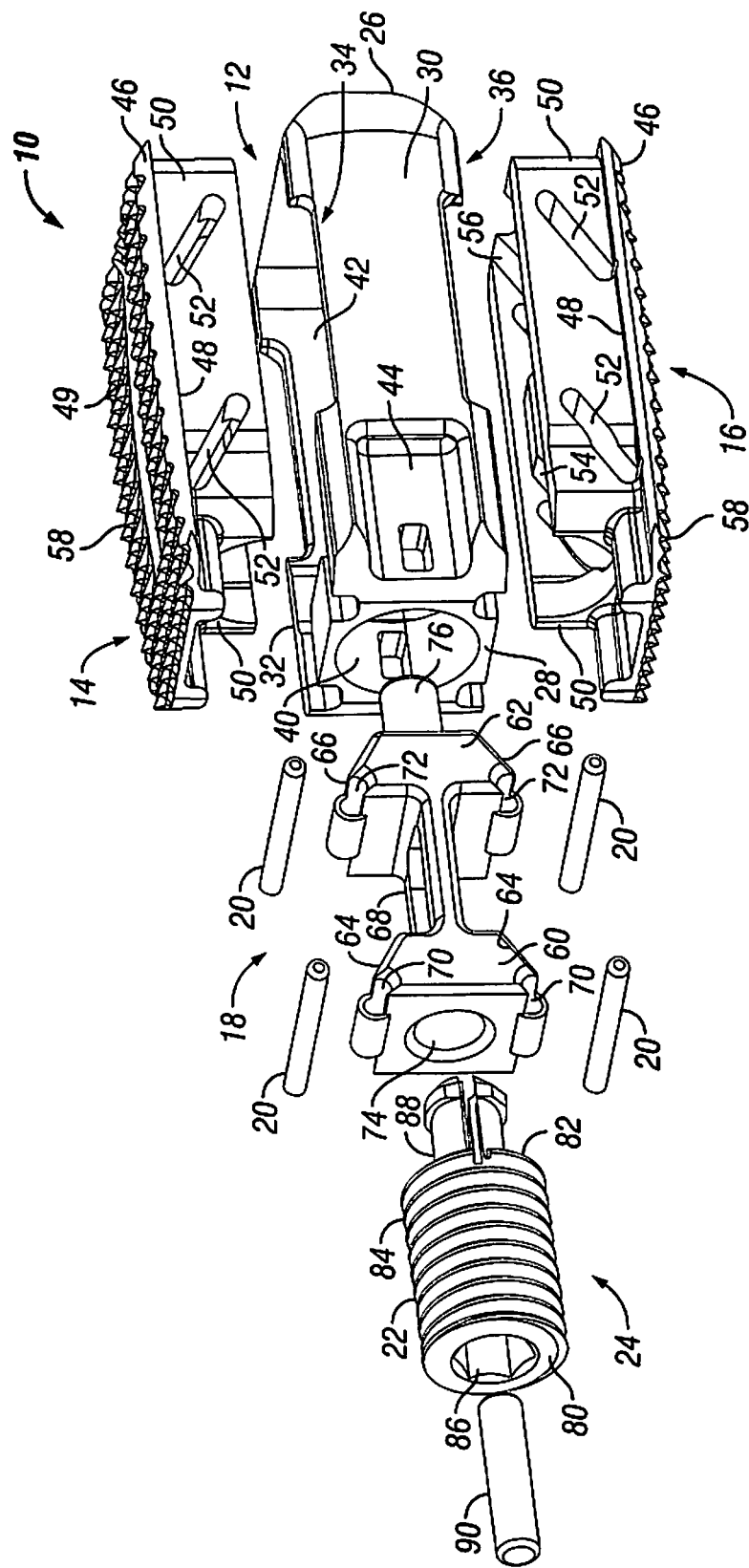
FIG. 2 is an exploded view of the expandable fusion device of FIG. 1.
Figure 3:
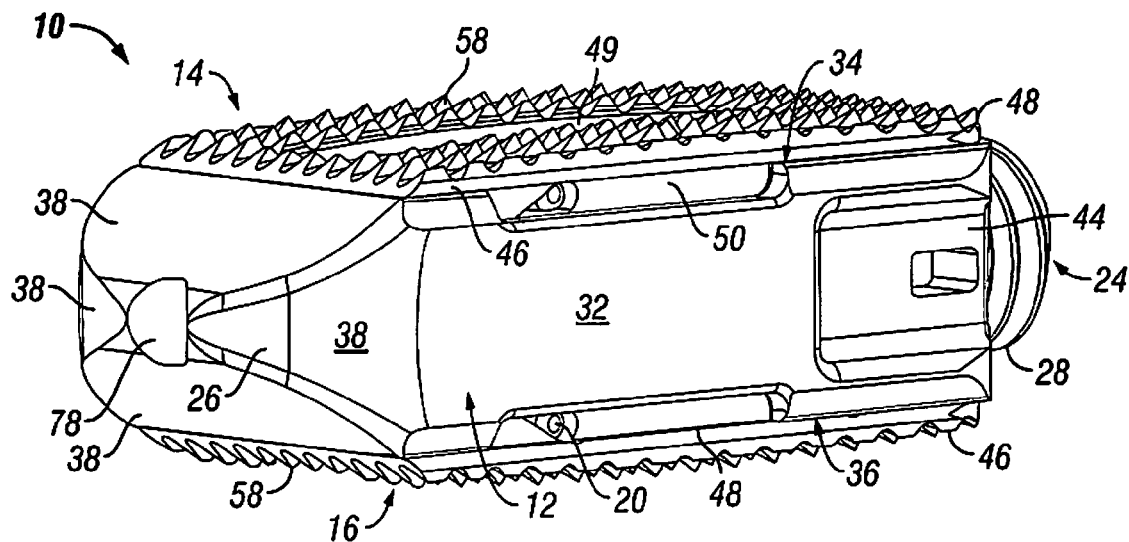
FIG. 3 is a front perspective view of the expandable fusion device of FIG. 1 shown in an unexpanded position

With reference to FIG. 2, an exploded perspective view of one embodiment of the fusion device 10 is shown. In an exemplary embodiment, the fusion device 10 includes a body portion 12, a first endplate 14, a second endplate 16, a translation member 18, a plurality of pins 20, an actuation member 22, and a locking mechanism 24.

With additional reference to FIGS. 3-8, in an exemplary embodiment, the body portion 12 has a first end 26, a second end 28, a first side portion 30 connecting the first end 26 and the second end 28, and a second side portion 32 connecting the first end 26 and the second end 28. The body portion 12 further includes an upper end 34, which is sized to receive at least a portion of the first endplate 14, and a lower end 36, which is sized to receive at least a portion of the second endplate 16.

The first end 26 of the fusion device 10, in an exemplary embodiment, includes at least one angled surface 38, but can include multiple angled surfaces. The angled surface can serve to distract the adjacent vertebral bodies when the fusion device 10 is inserted into an intervertebral space. In another preferred embodiment, it is contemplated that there are at least two opposing angled surfaces forming a generally wedge shaped to distract the adjacent vertebral bodies when the fusion device 10 is inserted into an intervertebral space.

The second end 28 of the body portion 12, in an exemplary embodiment, includes an opening 40 which may include threading. In another exemplary embodiment, the opening 40 may include ratchet teeth instead of threading. The opening 40 extends from the second end 28 of the body portion 12 into a central opening 42 in the body portion 12. In one embodiment, the central opening 42 is sized to receive the translation member 18 and the opening 40 is sized to threadingly receive the actuation member 22. In another exemplary embodiment, the opening 40 is sized to receive the actuation member 22 in a ratcheting fashion. In yet another exemplary embodiment, first side portion 30 and second side portion 32 each include a recess 44 located towards the second end 28 of the body portion 12. The recess 44 is configured and dimensioned to receive an insertion instrument (not shown) that assists in the insertion of the fusion device 10 into an intervertebral space.

Although the following discussion relates to the first endplate 14, it should be understood that it also equally applies to the second endplate 16 as the second endplate 16 is substantially identical to the first endplate 14. Turning now to FIGS. 2-11, in an exemplary embodiment, the first endplate 14 has an upper surface 46, a lower surface 48, and a through opening 49. The through opening 49, in an exemplary embodiment, is sized to receive bone graft or similar bone growth inducing material and further allow the bone graft or similar bone growth inducing material to be packed in the central opening 42 in the body portion 12.

Figure 4:
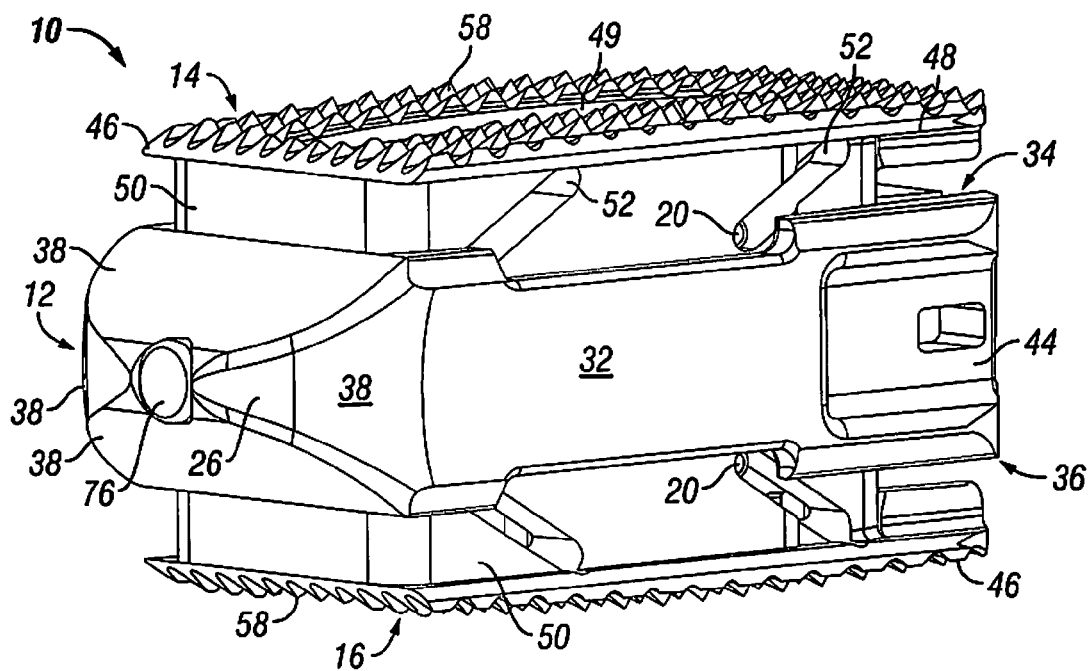
FIG. 4 is a front perspective view of the expandable fusion device of FIG. 1 shown in an expanded position.
Figure 5:
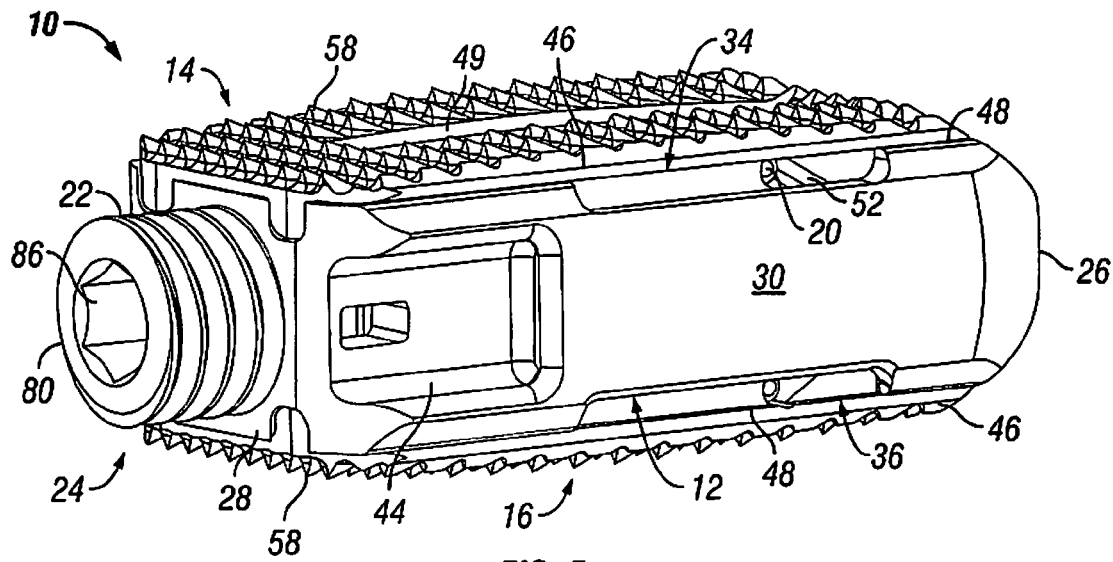
FIG. 5 is a rear perspective view of the expandable fusion device of FIG. 1 shown in an unexpanded position.
Figure 6:
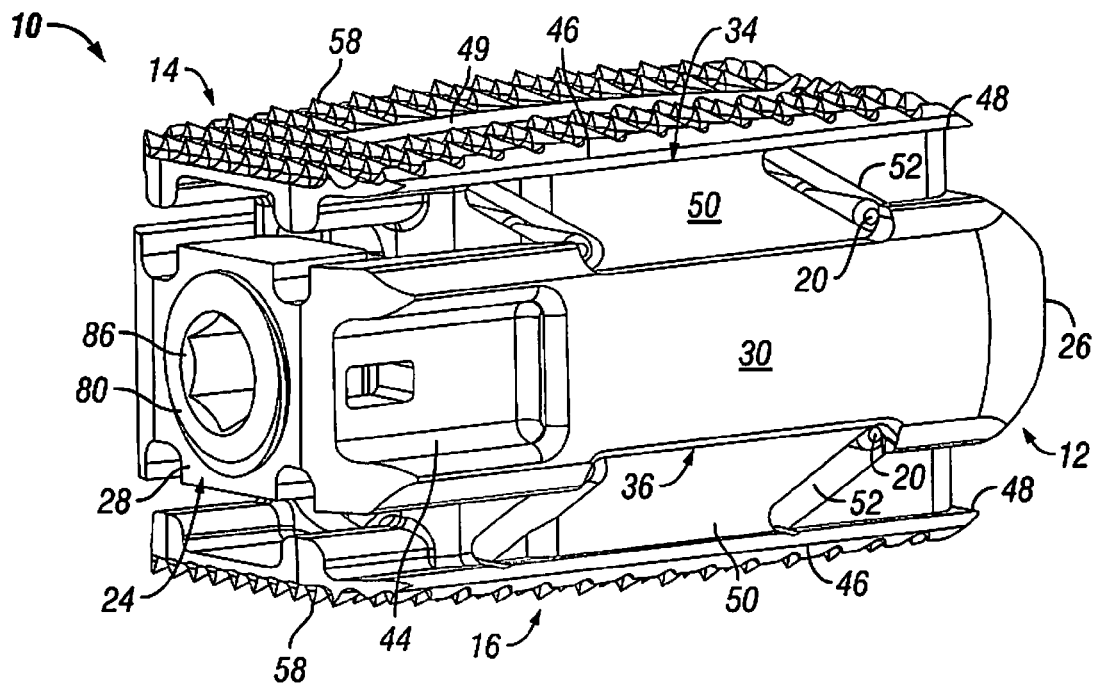
FIG. 6 is a rear perspective view of the expandable fusion device of FIG. 1 shown in an expanded position.
Figure 7:
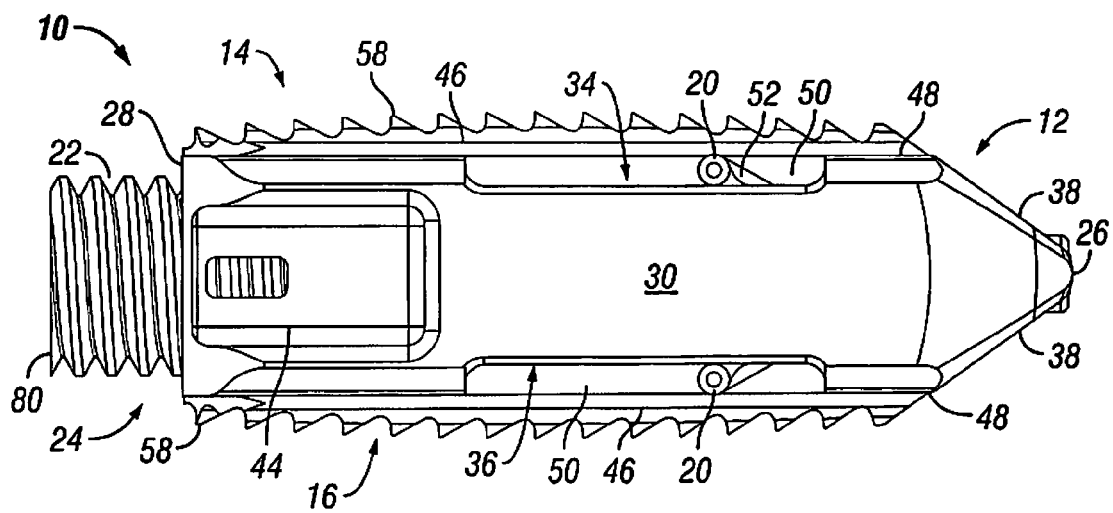
FIG. 7 is a side view of the expandable fusion device of FIG. 1 shown in an unexpanded position.
Figure 8:
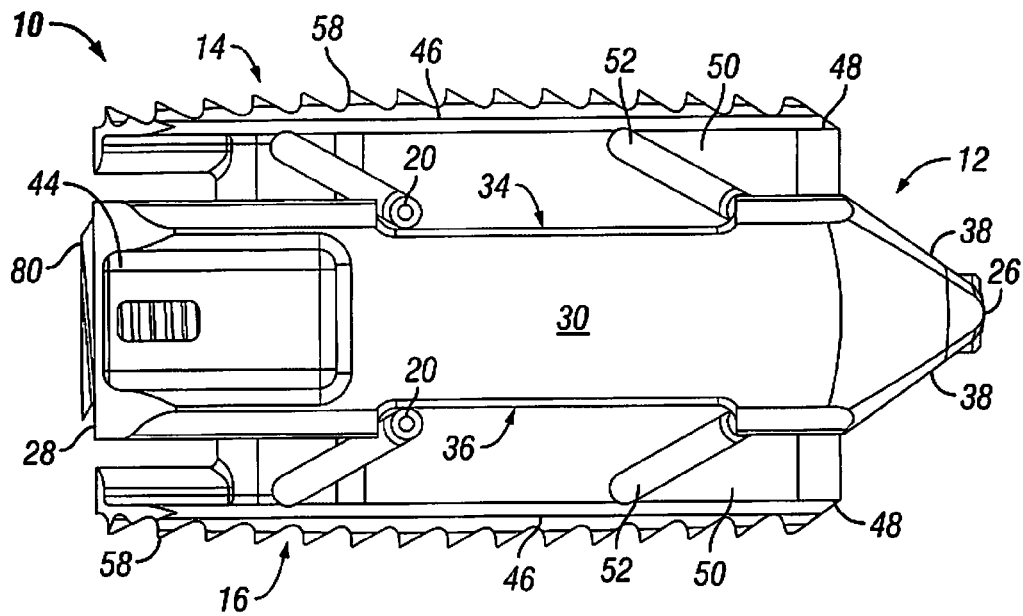
FIG. 8 is a side view of the expandable fusion device of FIG. 1 shown in an expanded position.
Figure 9:
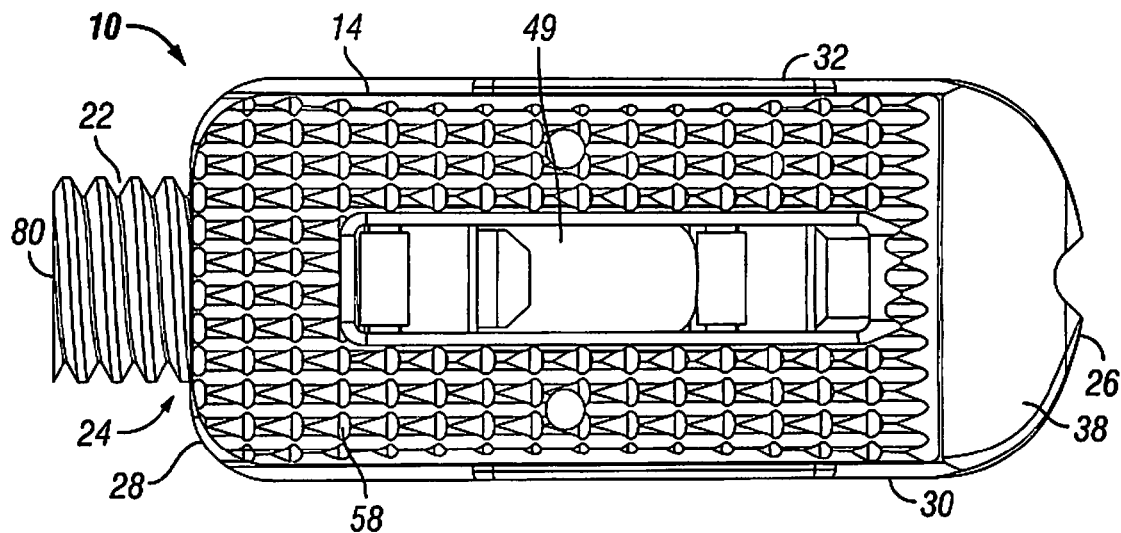
FIG. 9 is a top view of the expandable fusion device of FIG. 1.

In one embodiment, the lower surface 48 includes at least one extension 50 extending along at least a portion of the lower surface 48. As best seen in FIGS. 2 and 4, in an exemplary embodiment, the extension 50 can extend along a substantial portion of the lower surface 48, including, along each side of the endplate 14 and along the front end of the endplate 14. In another exemplary embodiment, the extension 50 includes at least one slot 52, but can include any number of slots 52, including two sets of slots 52 opposing each other, as best seen in FIG. 2. The slots 52 are configured and dimensioned to receive pins 20 and are oriented in an oblique fashion. In another embodiment, the slots 52 may be oriented in a generally vertical orientation.

Figure 12:
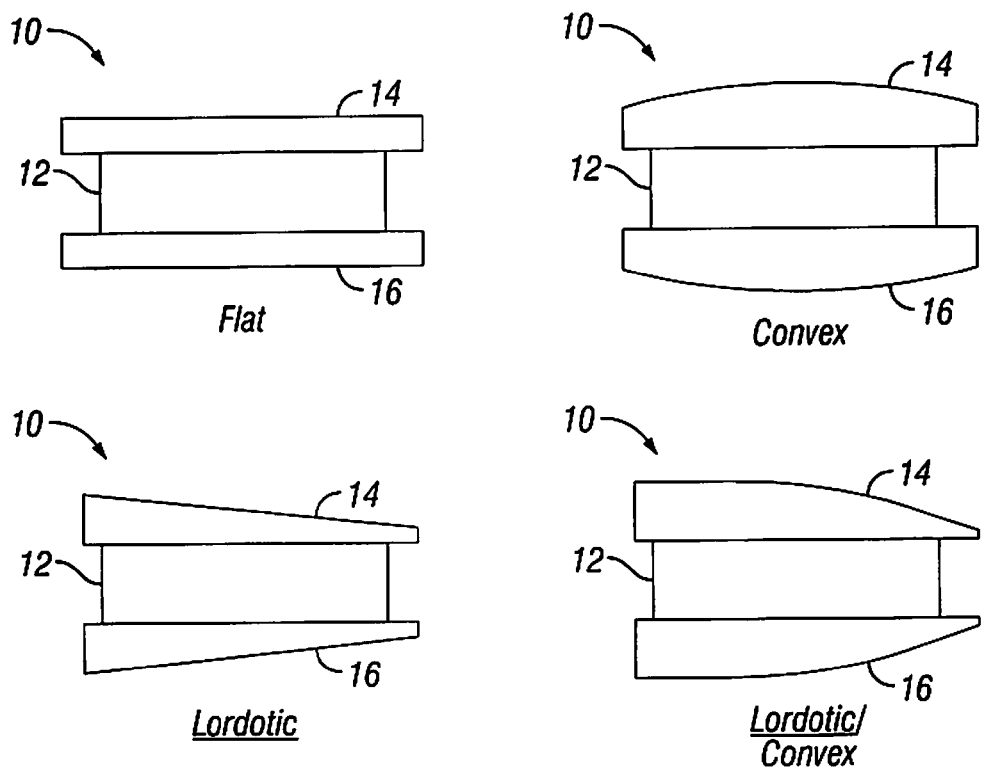
FIG. 12 is a side schematic view of the expandable fusion device of FIG. 1 having different endplates.
Figure 11:
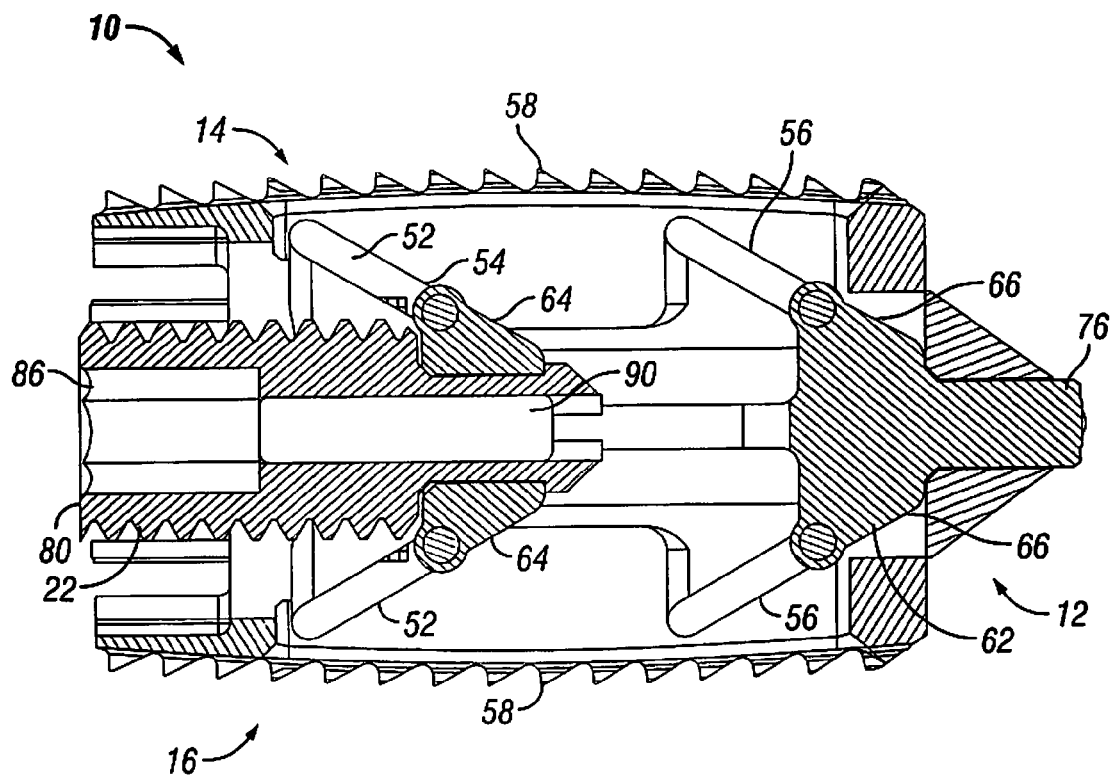
FIG. 11 is a side partial cross-sectional view of the expandable fusion device of FIG. 1 shown in an expanded position.

In an exemplary embodiment, the extension 50 is sized to be received within the central opening 42 of the body portion 12. As best seen in FIGS. 11-12, the lower surface 48 of the first endplate 14 further includes, in an exemplary embodiment, at least one ramped surface 54. In another exemplary embodiment, there are two spaced ramped surfaces 54, 56. It is contemplated that the slope of the ramped surfaces 54, 56 can be equal or can differ from each other. The effect of varying the slopes of the ramped surfaces 54, 56 is discussed below.

Referring now to FIGS. 2-9, in one embodiment, the upper surface 46 of the first endplate 14 is flat and generally planar to allow the upper surface 46 of the endplate 14 to engage with the adjacent vertebral body 2. Alternatively, as shown in FIG. 12, the upper surface 46 can be curved convexly or concavely to allow for a greater or lesser degree of engagement with the adjacent vertebral body 2. It is also contemplated that the upper surface 46 can be generally planar but includes a generally straight ramped surface or a curved ramped surface. The ramped surface allows for engagement with the adjacent vertebral body 2 in a lordotic fashion. Turning back to FIGS. 2-9, in an exemplary embodiment, the upper surface 46 includes texturing 58 to aid in gripping the adjacent vertebral bodies. Although not limited to the following, the texturing can include teeth, ridges, friction increasing elements, keels, or gripping or purchasing projections.

Figure 10:
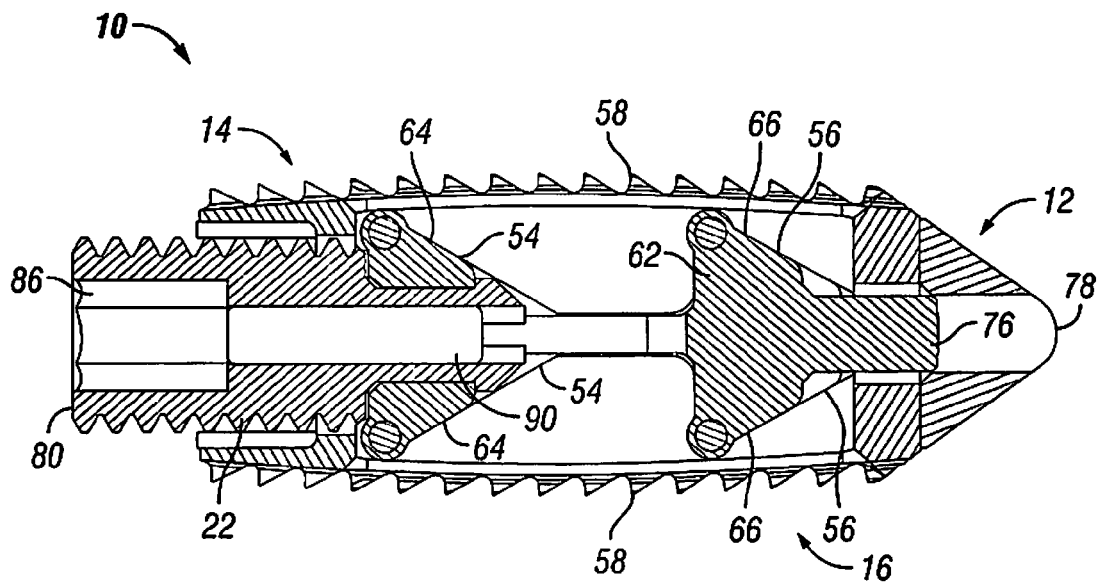
FIG. 10. is a side partial cross-sectional view of the expandable fusion device of FIG. 1 shown in an unexpanded position.

With reference to FIGS. 2 and 10-11, in an exemplary embodiment, the translation member 18 is sized to be received within the central opening 42 of the body portion 12 and includes at least a first expansion portion 60. In another embodiment, the translation member 18 includes a first expansion portion 60 and a second expansion portion 62, the expansion portions 60, 62 being connected together via a bridge portion 68. It is also contemplated that there may be more than two expansion portions where each of the expansion portions is connected by a bridge portion. The expansion portions 60, 62 each have angled surfaces 64, 66 configured and dimensioned to engage the ramp surfaces 54, 56 of the first and second endplates 14, 16. In an exemplary embodiment, the translation member 18 also includes recesses 70, 72, the recesses 70, 72 are sized to receive and retain pins 20. In one embodiment, the expansion portion 60 includes an opening 74, which is sized to receive a portion of the actuation member 22, and the expansion portion 62 includes a nose 76, which is received within an opening 78 in the first end 26 to stabilize the translation member 18 in the central opening 42 of the body member 12.

In an exemplary embodiment, the actuation member 22 has a first end 80, a second end 82 and threading 84 extending along at least a portion thereof from the first end 80 to the second end 82. The threading 84 threadingly engages the threading extending along a portion of opening 40 in the body portion 12. In another exemplary embodiment, the actuation member 22 includes ratchet teeth instead of threading. The ratchet teeth engage corresponding ratchet teeth in the opening 40 in the body portion 12. The first end 80 includes a recess 86 dimensioned to receive an instrument (not shown) that is capable of advancing the actuation member 22 with respect to the body portion 12 of the fusion device 10. The second end 82 of the actuation member 22 includes an extension 88 that is received within the opening 74 of the expansion portion 60. In one embodiment, the extension 88 may include a plurality of slits and a lip portion. The plurality of slits allows the extension portion 88 to flex inwardly reducing its diameter when received in the opening 74. Once the lip portion of the extension portion 88 is advanced beyond the end of the opening 74, the extension portion 88 will return back to its original diameter and the lip portion will engage the expansion portion 60. It is further contemplated that a pin member 90 can be included to prevent the extension portion from flexing inwardly thereby preventing the actuation member 22 from disengaging from the translation member 18.

In an exemplary embodiment, the fusion device 10 can further include a locking mechanism 24. The mechanism 24 is designed to resist rotation of the actuation member 22 rather than prevent rotation of the actuation member 22. In an exemplary embodiment, either deformable threading can be included on actuation member 22 or a disruption of the threading may be included where a deformable material is included in the threading disruption. It is contemplated that the deformable member or deformable threading can be made from a deformable or elastic, biocompatible material such as nitinol or PEEK.

Turning now to FIGS. 1-8 and 10-11, a method of installing the expandable fusion device 10 is now discussed. Prior to insertion of the fusion device 10, the intervertebral space is prepared. In one method of installation, a diskectomy is performed where the intervertebral disc, in its entirety, is removed. Alternatively, only a portion of the intervertebral disc can be removed. The endplates of the adjacent vertebral bodies 2, 3 are then scraped to create an exposed end surface for facilitating bone growth across the invertebral space. The expandable fusion device 10 is then introduced into the intervertebral space, with the first end 26 being inserted first into the disc space followed by the second end 28. In an exemplary method, the fusion device 10 is in the unexpanded position when introduced into the intervertebral space. The wedged shaped first end 26 will assist in distracting the adjacent vertebral bodies 2, 3 if necessary. This allows for the option of having little to no distraction of the intervertebral space prior to the insertion of the fusion device 10. In another exemplary method, the intervertebral space may be distracted prior to insertion of the fusion device 10. The distraction provide some benefits by providing greater access to the surgical site making removal of the intervertebral disc easier and making scraping of the endplates of the vertebral bodies 2, 3 easier.

With the fusion device 10 inserted into and seated in the appropriate position in the intervertebral disc space, the fusion device can then expanded into the expanded position, as best seen in FIGS. 1, 4, 6, 8, and 11. To expand the fusion device 10, an instrument is engaged with recess 86 in the actuation member 22. The instrument is used to rotate actuation member 22. As discussed above, actuation member 22 is threadingly engaged body portion 12 and is engaged with translation member 18; thus, as the actuation member 22 is rotated in a first direction, the actuation member 22 and the translation member 18 move with respect to the body portion 12 toward the first end 26 of the body portion 12. In another exemplary embodiment, the actuation member 22 is moved in a linear direction with the ratchet teeth engaging as means for controlling the movement of the actuation member 22 and the translation member 18. As the translation member 18 moves, the ramped surface 64, 66 of the expansion portions 60, 62 push against the ramped surfaces 54, 56 of the endplates 14, 16 pushing endplates 14, 16 outwardly into the expanded position. This can best be seen in FIGS. 10 and 11. Since the expansion of the fusion device 10 is actuated by a rotational input, the expansion of the fusion device 10 is infinite. In other words, the endplates 14, 16 can be expanded to an infinite number of heights dependent on the rotational advancement of the actuation member 22. As discussed above, the fusion device 10 includes a locking mechanism 24 which assists in retaining the endplates 14, 16 at the desired height.

Figure 13:
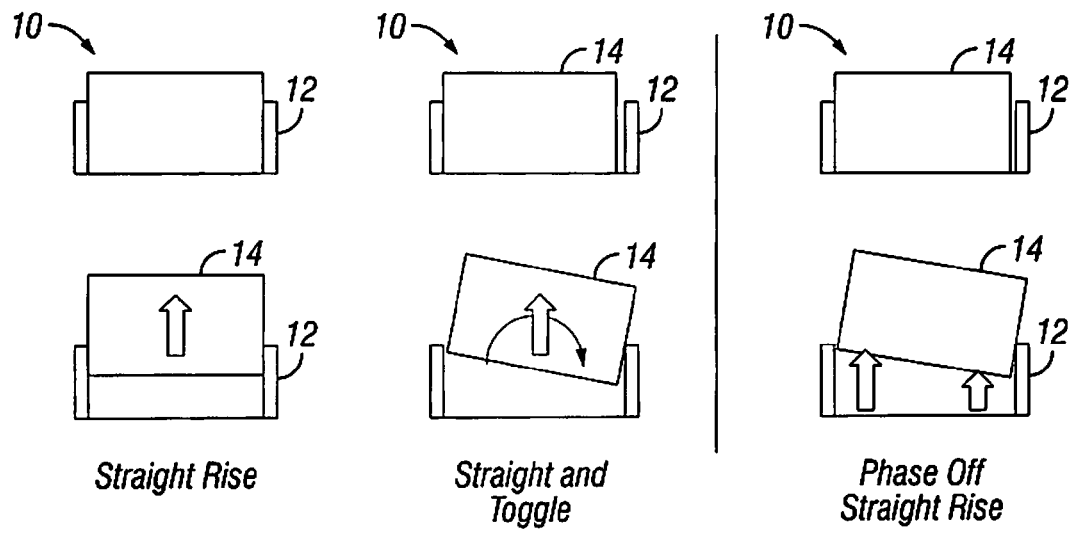
FIG. 13 is a partial side schematic view of the expandable fusion device of FIG. 1 showing different modes of endplate expansion.

It should also be noted that the expansion of the endplates 14, 16 can be varied based on the differences in the dimensions of the ramped surfaces 54, 56, 64, 66. As best seen in FIG. 13, the endplates 14, 16 can be expanded in any of the following ways: straight rise expansion, straight rise expansion followed by a toggle into a lordotic expanded configuration, or a phase off straight rise into a lordotic expanded configuration.

Turning back to FIGS. 1-8 and 10-11, in the event the fusion device 10 needs to be repositioned or revised after being installed and expanded, the fusion device 10 can be contracted back to the unexpanded configuration, repositioned, and expanded again once the desired positioning is achieved. To contract the fusion device 10, the instrument is engaged with recess 86 in the actuation member 22. The instrument is used to rotate actuation member 22. As discussed above, actuation member 22 is threadingly engaged body portion 12 and is engaged with translation member 18; thus, as the actuation member 22 is rotated in a second direction, opposite the first direction, the actuation member 22 and translation member 18 move with respect to the body portion 12 toward the second end 28 of the body portion 12. As the translation member 18 moves, the pins 20, a portion of which are located within the slots 52, ride along the slots 52 pulling the endplates 14, 16 inwardly into the unexpanded position.

Figure 14:
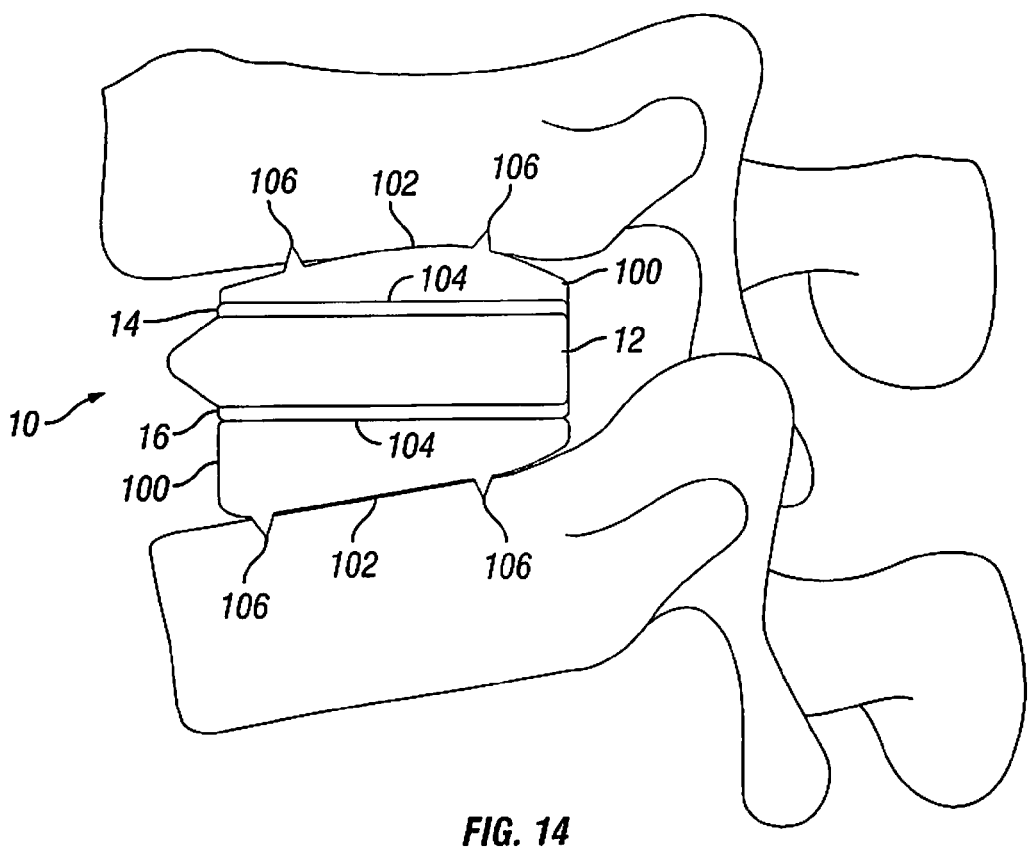
FIG. 14 is a side schematic view of the expandable fusion device of FIG. 1 with artificial endplates shown between adjacent vertebrae.

With reference now to FIG. 14, fusion device 10 is shown with an exemplary embodiment of artificial endplates 100. Artificial endplates 100 allows the introduction of lordosis even when the endplates 14 and 16 of the fusion device 10 are generally planar. In one embodiment, the artificial endplates 100 have an upper surface 102 and a lower surface 104. The upper surfaces 102 of the artificial endplates 100 have at least one spike 106 to engage the adjacent vertebral bodies. The lower surfaces 104 have complementary texturing or engagement features on their surfaces to engage with the texturing or engagement features on the upper endplate 14 and the lower endplate 16 of the fusion device 10. In an exemplary embodiment, the upper surface 102 of the artificial endplates 100 have a generally convex profile and the lower surfaces 104 have a generally parallel profile to achieve lordosis. In another exemplary embodiment, fusion device 10 can be used with only one artificial endplate 100 to introduce lordosis even when the endplates 14 and 16 of the fusion device 10 are generally planar. The artificial endplate 100 can either engage endplate 14 or engage endplate 16 and function in the same manner as described above with respect to two artificial endplates 100.

Although the preceding discussion only discussed having a single fusion device 10 in the intervertebral space, it is contemplated that more than one fusion device 10 can be inserted in the intervertebral space. It is further contemplated that each fusion device 10 does not have to be finally installed in the fully expanded state. Rather, depending on the location of the fusion device 10 in the intervertebral disc space, the height of the fusion device 10 may vary from unexpanded to fully expanded.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An intervertebral implant comprising:
   a first endplate having an upper side and a lower side, wherein the lower side of the first endplate includes a plurality of ramped surfaces extending therefrom;
   a second endplate having an upper side and a lower side;
   a body portion having a first end, a second end, a first side portion connecting the first end and the second end, and a second side portion connecting the first end and the second end, wherein the first end plate and the second endplate are received within the body;
   a translation member receivable in the body portion, the translation member including a first expansion portion having an angled surface configured to engage one ramped surface extending from the first endplate and a second expansion portion having an angled surface configured to engage another of the ramped surfaces extending from the first endplate; and an actuation member comprising a threaded member, wherein the actuation member is non-threadably engaged with the translation member, wherein rotation of the actuation member causes translational movement of the translation member, and
   wherein movement of the translation member causes the first expansion portion and second expansion portion to move from the first end of the body portion to the second end of the body portion causing the angled surface of the first expansion portion to push against one ramped surface extending from the first endplate and the angled surface of the second expansion portion to push against another ramped surface extending from the first endplate, thereby causing outward expansion of the first endplate.

2. The implant of claim 1, wherein the first endplate includes a pair of ramped surfaces.

3. The implant of claim 1, wherein the translation member comprises a pair of ramped surfaces connected by a bridge portion.

4. The implant of claim 1, wherein the translation member includes a central opening.

5. An intervertebral implant comprising:
   a first endplate having an upper side and a lower side, wherein the lower side of the first endplate includes ramped surfaces extending therefrom, wherein the upper side includes an opening therethrough;
   a second endplate having an upper side and a lower side, wherein the upper side of the second endplate includes at least one ramped surface extending therefrom;
   a body portion having a first end, a second end, a first side portion connecting the first end and the second end, and a second side portion connecting the first end and the second end, wherein the first end plate and the second endplate are received within the body; and
   a translation member receivable in the body portion, the translation member having an upper surface and a lower surface, the upper surface of the translation member including a first angled surface and a second angled surface, each which is configured to engage at least one of the ramped surfaces extending from the first endplate and the lower surface of the translation member includes a third and fourth angled surface, at least one of the third and fourth angled surface configured to engage the at least one ramped surface extending from the second endplate; and an actuation member comprising a threaded member, wherein the actuation member is non-threadably engaged with the translation member, and wherein rotation of the actuation member causes translational movement of the translation member such that the first and second angled surfaces are moved from the first end of the body portion to the second end of the body portion.

6. The implant of claim 5, wherein the first endplate includes at least two ramped surfaces.

7. The implant of claim 6, wherein the slope of the at least two ramped surfaces is different from one another.

8. The implant of claim 5, wherein movement of the translation member causes the first angled surface to push against at least one of the ramped surfaces extending from the first endplate and the third angled surface to push against the at least one ramped surface extending from the second endplate, thereby causing outward expansion of the first endplate and second endplate.

9. The implant of claim 5, wherein the first end of the body portion includes at least one angled surface to assist in distraction of vertebral bodies.

10. An intervertebral implant comprising:
    a first endplate having an upper side and a lower side, wherein the lower side of the first endplate includes first and second ramped surfaces extending therefrom;
    a second endplate having an upper side and a lower side, wherein the upper side of the second endplate includes first and second ramped surfaces extending therefrom body portion having a first end, a second end, a first side portion connecting the first end and the second end, and a second side portion connecting the first end and the second end, wherein the first end plate and the second endplate are received within the body;
    a translation member including a first expansion portion having a first angled surface configured to engage the first ramped surface extending from the first endplate and a second angled surface configured to engage the first ramped surface extending from the second endplate and a second expansion portion having a first angled surface configured to engage the second ramped surface extending from the first endplate and a second angled surface configured to engage the second ramped surface extending from the second endplate,
    an actuation member comprising a threaded member, wherein the actuation member is non-threadably engaged with the translation member, and wherein rotation of the actuation member causes translational movement of the translation member,
    wherein movement of the translation member causes the first expansion portion and second expansion portions to move from the first end of the body portion to the second end of the body portion causing the first angled surface of the first expansion portion to push against the first ramped surface extending from the first endplate and the second angled surface of the first expansion portion to push against the first ramped surface extending from the second endplate and causing the first angled surface of the second expansion portion to push against the second ramped surface extending from the first endplate and the second angled surface of the second expansion portion to push against the second ramped surface extending from the second endplate thereby causing outward expansion of the first endplate and the second endplate.

11. The implant of claim 10, wherein the body portion comprises an angled surface to assist in distraction of vertebral bodies during insertion of the implant.

12. The implant of claim 10, wherein the first and second expansion portions of the translation member are separated by a bridge member.

13. The implant of claim 10, wherein the translation member includes a central hole.

* * * * *